(12) United States Patent
Feiertag et al.

(10) Patent No.: US 8,579,440 B2
(45) Date of Patent: Nov. 12, 2013

(54) EYESIGHT TESTING APPARATUS

(75) Inventors: Carsten Feiertag, Hungen (DE); Rainer Kirchhuebel, Asslar (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 83 days.

(21) Appl. No.: 13/249,656

(22) Filed: Sep. 30, 2011

(65) Prior Publication Data

US 2012/0081669 A1  Apr. 5, 2012

(30) Foreign Application Priority Data

Sep. 30, 2010 (DE) .................... 20 2010 013 741 U
Aug. 17, 2011 (EP) ..................................... 11177792

(51) Int. Cl.
*A61B 3/032* (2006.01)
*A61B 3/10* (2006.01)

(52) U.S. Cl.
CPC .. *A61B 3/032* (2013.01); *A61B 3/10* (2013.01)
USPC ............ 351/237; 351/211; 351/221; 351/243

(58) Field of Classification Search
USPC .................................. 351/207, 220, 232, 237
See application file for complete search history.

(56) References Cited

U.S. PATENT DOCUMENTS

| | | | | |
|---|---|---|---|---|
| 4,452,517 A | * | 6/1984 | Kohayakawa | 351/206 |
| 5,793,469 A | * | 8/1998 | Feiertag et al. | 351/221 |
| 5,870,168 A | * | 2/1999 | Kirchhuebel et al. | 351/221 |
| 7,241,011 B2 | * | 7/2007 | Baek et al. | 351/206 |

FOREIGN PATENT DOCUMENTS

| | | |
|---|---|---|
| CN | 101556402 A | 10/2009 |
| DE | 4 036 964 A1 | 5/1992 |
| DE | 41 13 536 A1 | 11/1992 |
| DE | 42 22 100 C2 | 1/1994 |
| DE | 195 01 415 A1 | 1/1995 |
| DE | 103 10 589 B4 | 8/2004 |
| EP | 0 487 073 A1 | 5/1992 |
| JP | 8229003 A | 9/1996 |
| JP | 2003180633 | 7/2003 |

OTHER PUBLICATIONS

Search Report issued in corresponding European application 111777926.6, completed Jan. 5, 2012 and mailed Jan. 16, 2012.
Office Action of Japanese Patent and Trademark Office relating to parallel application No. 2011-214004, dated Jan. 22, 2013 and mailed Feb. 1, 2013.

* cited by examiner

*Primary Examiner* — Ricky Mack
*Assistant Examiner* — William Alexander
(74) *Attorney, Agent, or Firm* — Griffin & Szipl, P.C.

(57) ABSTRACT

An eyesight testing apparatus includes an imaging device for virtual imaging a test object located within a focal length of the imaging device and imaged at different distances into eyes of a subject located in a focal point of the imaging device, an optical deflection device arranged in a beam path between the imaging device and the test object to deflect the beam path by 180°, wherein the deflection device is displaceable in the direction of the beam path and the test object is not, a monitor device that generates the test object and that comprises a single monitor, optical components lying in the beam path sized so that both eyes are able to take part in a test, and so a partial beam path is formed for each eye, and a blocking device arranged in the beam path, which comprises two LCD blocking elements for the partial beam paths.

17 Claims, 4 Drawing Sheets

US 8,579,440 B2

EYESIGHT TESTING APPARATUS

This application claims priority from German Utility Model Patent Application No. 20 2010 013 741.1, filed Sep. 30, 2010, and from European Patent Application No. 11177792.6, filed Aug. 17, 2011, the entire disclosures of which are incorporated herein by reference.

FIELD OF THE INVENTION

The invention relates to an eyesight testing apparatus comprising an imaging device for the virtual imaging of a test object, which is located within a focal length of the imaging device and can be imaged at different distances, into an eye of a subject located in a focal point of the imaging device, comprising an optical deflection device, wherein the deflection device is arranged in a beam path between the imaging device and the test object and deflects the beam path by 180°, wherein the deflection device is displaceable in the direction of the beam path, and wherein the test object is not displaceable, comprising a monitor device, wherein the monitor device generates the test object, wherein the monitor device comprises a single monitor, wherein the optical components lying in the beam path are of such a size that both eyes of the subject are able to take part in the test, and wherein a partial beam path can thus be formed for each eye.

BACKGROUND OF THE INVENTION

Such eyesight testing apparatuses are sufficiently known from the prior art and basically carry out different eyesight tests on a subject. In particular, a separation of the beam path into partial beam paths for each eye makes it possible to carry out a binocular eyesight test, for example to examine the stereoscopic vision. For this purpose a different test object for each partial beam path is shown to the subject. This may be achieved in that a separate monitor for showing the test object is used for each partial beam path. However, a drawback is that the two monitors have to be aligned, at a distance from one another, with a pupil distance of the subject. Since pupil distances of different subjects can deviate from one another, in this case an eyesight test is inaccurate.

Eyesight testing arrangements, which are formed of a monitor or a visual display unit and test spectacles worn by a subject, are also known. The visual display unit and the test symbols shown thereby as well as the respective lenses of the test spectacles assigned to the eyes are polarised differently so that the subject sees a different test object with each eye. Drawbacks of this are that assembly of this eyesight testing apparatus requires a relatively large amount of space owing to a necessary distance from the visual display unit, and that it is not possible to readily carry out reliable eyesight tests quickly for different viewing distances. It is also not possible to objectively examine both eyes separately from one another since the subject always notices which of its eyes is covered. A subject can thus very easily also simulate an ametropia without this being realised.

The object of the present invention is therefore to propose an eyesight test device that is compact and can be handled easily, and with which a maximum number of different eyesight tests can be carried out without the aforementioned limitations.

SUMMARY OF THE INVENTION

This object of the invention is achieved by a first embodiment of the invention, which pertains to an eyesight testing apparatus (10, 35) including: (a) an imaging device (15) for the virtual imaging of a test object, which is located within a focal length of the imaging device and can be imaged at different distances, into an eye (11, 12) of a subject located in a focal point of the imaging device, comprising an optical deflection device (19), wherein the deflection device is arranged in a beam path (13, 14) between the imaging device and the test object and deflects the beam path by 180 degrees, wherein the deflection device is displaceable in the direction of the beam path, and the test object is not displaceable, and the eyesight testing apparatus further comprises (b) a monitor device (21), wherein the monitor device generates the test object, and the monitor device comprises a single monitor (22), (c) the optical components (16, 17, 18, 19, 23) lying in the beam path that are of such a size that both eyes of the subject are able to take part in the test, it thus being possible for a partial beam path (13; 14) to be formed for each eye, and wherein (d) a blocking device (30) is arranged in the beam path, the blocking device comprising two LCD blocking elements (31, 32) that are assigned to each of the partial beam paths. In accordance with a second embodiment of the present invention, the first embodiment is modified so that a partial beam path (13; 14) can be visually blocked selectively by means of the blocking device (30).

In accordance with a third embodiment of the present invention, the first embodiment or the second embodiment are further modified so that two visually different test objects can be displayed at the same time in a discernible manner by means of the monitor (22), wherein the respective partial beam paths (13; 14) are synchronously blockable or releasable by means of the LCD blocking elements (31, 32) with a change of a display of the test objects on the monitor. In accordance with a fourth embodiment of the present invention, the first embodiment, the second embodiment and the third embodiment are further modified so that the monitor (22) is an LCD or an LED monitor.

In accordance with a fifth embodiment of the present invention, the first embodiment, the second embodiment, the third embodiment, and the fourth embodiment are further modified so that the imaging device (15) comprises a diverting element (18) for diverting the beam path (13, 14). In accordance with a sixth embodiment of the present invention, the fifth embodiment is further modified so that the diverting element (18) is adjustable in such a way that the beam path (13; 14) incident in the eye (11, 12) can be inclined relative to a horizontal optical axis (34) of the eye about an angle α. In accordance with a seventh embodiment of the present invention, the fifth embodiment and the sixth embodiment are further modified so that a viewing opening in the eyesight testing apparatus (10, 35) can be vertically adjusted relative to an installation surface of the eyesight testing apparatus. In accordance with an eighth embodiment of the present invention, the fifth embodiment, the sixth embodiment and the seventh embodiment are further modified so that the blocking device (30) is arranged in the beam path (13; 14) between the diverting element (18) and a lens group (16, 17) of the imaging device (15).

In accordance with a ninth embodiment of the present invention, the first embodiment, the second embodiment, the third embodiment, the fourth embodiment, the fifth embodiment, the sixth embodiment, the seventh embodiment, and the eighth embodiment are further modified so that the monitor device (21) comprises an illumination unit (25, 39) for the test object. In accordance with a tenth embodiment of the present invention, the ninth embodiment is further modified so that the illumination unit (25, 39) comprises an LED light source (26) and a collimator (27). In accordance with an eleventh embodiment of the present invention, the tenth embodiment is further modified so that the LED light source (26) comprises at least one RGBW LED. In accordance with a twelfth embodiment of the present invention, the ninth embodiment, the tenth embodiment and the eleventh embodiment are further modified so that the monitor device (21) comprises a beam splitter (23) that is arranged in the beam path (13; 14) between the monitor (22) and the illumination unit (25, 39). In accordance with a thirteenth embodiment of the present invention, the twelfth embodiment is further modified so that the beam splitter (23) forms a polariser.

In accordance with a fourteenth embodiment of the present invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, and the thirteenth embodiment, are further modified so that the monitor device (21) comprises a glare source (24, 36) which can be imaged in the eye (11, 12) of the subject together with the test object. In accordance with a fifteenth embodiment of the present invention, the fourteenth embodiment is further modified so that the glare source (36) is arranged in an imaging plane of the monitor (22). In accordance with a sixteenth embodiment of the present invention, the fourteenth embodiment and the fifteenth embodiment are further modified so that the glare source (36) comprises a polariser. In accordance with a seventeenth embodiment of the present invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment, the thirteenth embodiment, the fourteenth embodiment, the fifteenth embodiment, and the sixteenth embodiment are further modified so that the eyesight testing apparatus (10, 35) comprises a control device with which the monitor (22) and the blocking means (30) can be controlled.

The eyesight testing apparatus, according to the invention, comprises an imaging device for the virtual imaging of a test object, which is located within a focal length of the imaging device and can be imaged at different distances, into an eye of a subject located in a focal point of the imaging device, an optical deflection device, wherein the deflection device is arranged in a beam path between the imaging device and the test object and deflects the beam path by 180°, wherein the deflection device is displaceable in the direction of the beam path, and wherein the test object is not displaceable, a monitor device, wherein the monitor device generates the test object, wherein the monitor device comprises a single monitor, wherein the optical components lying in the beam path are of such a size that both eyes of the subject are able to take part in the test, wherein a partial beam path can thus be formed for each eye, and wherein a blocking device is arranged in the beam path, wherein the blocking device comprises two LCD blocking elements that are assigned to each of the partial beam paths.

In particular, the use of the displaceable deflection device makes it possible to carry out eyesight tests in a simple manner at different eyesight distances for close vision and far vision. The eyesight testing apparatus can also be formed in a comparatively compact manner owing to the deflection of the beam path and therefore can be easily transported and handled. In the present case all components of the eyesight testing apparatus are further arranged in a housing thereof. Owing to the use of a single monitor for both partial beam paths, it is no longer necessary to adapt a pupil distance and variable pupil distances of subjects can be disregarded. "LCD shutters" are used as liquid crystal display (LCD) blocking elements (liquid crystal display blocking elements), and are connected to the monitor for synchronous control and block or release the respective partial beam paths. It is thus possible for the respective partial beam paths to show different test objects using the one monitor without having to use a colour display of the test objects. Owing to an interaction between the aforementioned components of the eyesight testing apparatus, a range of further eyesight tests can be carried out, for example a test of colour vision, monocular and binocular visual acuity, simultaneous binocular vision, stereoscopic vision, field of vision, reaction and basic ametropias such as myopia, hyperopia or presbyopia. In particular, it is now possible by use of the monitor to display any number of optotypes and to carry out dynamic eyesight tests.

In one embodiment of the eyesight testing apparatus, a partial beam path can be visually blocked selectively by means of the blocking device. It is thus possible by means of the eyesight testing apparatus to carry out a monocular eyesight test. A partial beam path can thus be blocked in a simple manner since the relevant LCD blocking element is completely shaded. This can be achieved in that the LCD blocking element carries out two linear polarisations, formed perpendicular to one another, of the respective partial beam path.

Two visually different test objects can also be displayed at the same time in a discernible manner by means of the monitor when, by means of the LCD blocking elements or the LCD shutters, the partial beam paths can be synchronously blocked or released, a display of the test objects on the monitor being changed. Alternatively, the visually different test objects can each be displayed at the same time with different polarisation by means of the monitor, wherein the respective partial beam paths are differently polarised by means of the LCD blocking elements. The partial beam paths can thus also be blocked or released synchronously with a change of the test objects on the monitor. It is thus possible to carry out a binocular eyesight test in which the subject is shown different teat objects for each partial beam path. The test objects can be displayed by the monitor in alternation with a frequency above a flicker fusion frequency of the eye, wherein the LCD blocking elements block or release the partial beam paths differently so that in each case only one of the test objects can be viewed by a partial beam path.

In order to simplify the eyesight testing apparatus, the monitor may be a liquid crystal display (LCD) or light-emitting diode (LED) monitor. Such monitors are small in size and can be easily integrated into an eyesight testing apparatus at almost any point. For example, if necessary a desired polarisation of the beam path can also be set by the LCD monitor. A test object that is already illuminated can be displayed by means of the LED monitor.

In order to form the eyesight testing apparatus in a compact manner and to be able to easily adapt it to a height of a subject, for example, who is sitting down, the imaging device may comprise a diverting element for diverting the beam path. It is thus possible to construct the eyesight testing apparatus with a substantially vertical beam path that can be deflected in the direction of a substantially horizontal line of vision of a subject. To form the eyesight testing apparatus a space is then provided between a horizontal line of vision of a subject who is sitting down and a table surface for installation of the eyesight testing apparatus.

The diverting element can be formed so as to be adjustable in such a way that the beam path incident into the eye can be inclined relative to a horizontal optical axis of the eye about an angle α. Since, for physiological reasons, in the case of far vision the optical axis of the eye approximates a horizontal optical axis and in the case of close vision is automatically inclined relative to the horizontal optical axis of the subject, the eyesight testing apparatus can be easily adapted to the respectively altered optical axis by inclining or adjusting the diverting element. In the case of far vision the diverting element can thus be raised in height so that a horizontal optical axis is basically achieved, and in the case of close vision the diverting element is lowered to such an extent towards a table surface that the optical axis is inclined towards the table surface comparatively sharply relative to the horizontal optical axis.

Further, a viewing opening into eyesight testing apparatus can be vertically adjustable relative to an installation surface of the eyesight testing apparatus. A vertically adjustable viewing opening is advantageous since, if an optical axis of an eye is to be inclined relative to a horizontal optical axis, in particular if an optical axis is inclined downwards towards a table surface, the height of the viewing opening can advantageously be reduced. If, in the case of this adjustment of the eyesight testing apparatus, a close vision of the subject is examined, a length of the beam path can simultaneously be shortened by displacement of the deflection device in the vertical direction so that, overall, the height of the eyesight testing apparatus can advantageously be reduced during this eyesight test. The adjustment of the diverting element in a height relative to the eye of the subject may be accompanied by a simultaneous pivoting or rotation of the diverting element so as to adapt the beam path to the altered optical axis.

It is particularly advantageous if the blocking device is arranged in the beam path between the diverting element and a lens group of the imaging device. The subject then cannot readily identify which of the two LCD blocking elements is completely closed since the LCD blocking elements are not arranged in the vicinity of the eyes of the subject, but inside an apparatus housing of the eyesight testing apparatus. It is therefore no longer possible for the subject to unknowingly influence an eyesight test or to simulate a visual defect, since he cannot readily identify which of the two eyes is being tested.

In terms of an illumination of the monitor, it is advantageous if the monitor device comprises an illumination unit for the test object. For example, the illumination unit may provide an epi-illumination of the test object.

The illumination unit may thus comprise an LED light source and a collimator. An LED light source can be miniaturised in a particularly simple manner and generates hardly any thermal energy, which would have to be removed. The LED light source may comprise a plurality of light diodes, of which the light is guided through the collimator onto the test object. The light diodes may have different colours or light colours that can be varied depending on the desired eyesight test.

It is particularly advantageous if the LED light source comprises at least one RGBW LED (red-green-blue-white LED). Such an LED provided with four chips makes it possible to illuminate the test object in a manner particularly adapted to the respective eyesight test. The RGB chips (red-green-blue chips) of the LED may thus be used for an illumination of the test object in a light environment, and the white chip may be used for an illumination of the test object in a mesopic, dark environment. The RGB chips have good colour rendering properties with high luminous efficacy. By contrast, the white chip is suitable for generation of lower illumination strengths.

The monitoring device may comprise a beam splitter, which is arranged in the beam path between the monitor and the illumination unit. The beam splitter may be formed as a beam-splitting prism having a half-silvered mirror, or as a half-silvered mirror solely. The half-silvered mirror may thus have an angle of 45° relative to a vertical beam path of the eyesight testing apparatus so that the monitor and the illumination unit can each be arranged opposite the beam splitter in a horizontal beam path thereof. A particularly compact structure of the eyesight testing apparatus is thus also possible.

Further, the beam splitter may form a polariser or a polarising beam splitter. Inter alia, it is thus also possible to set specific splitter ratios of the beam splitter. Two polarised light beams can also be combined so as to achieve a greater output, or the beam path can be polarised for a desired interaction with the blocking device.

For example, in order to simulate a glaring of an eye, the monitor device may comprise a glare source, which can be imaged together with the test object in the eye of the subject. In the simplest embodiment the glare source may be formed as a light diode that is arranged relative to the beam path of the eyesight testing apparatus in such a way that a glaring effect of the eye can be achieved. It is thus also possible to arrange the glare source in the region of a beam splitter of the monitor device and to thus couple a glare generated by the glare source into the beam path.

It is particularly advantageous if the glare source is arranged in an imaging plane of the monitor. It is thus possible to arrange the glare, which may be produced by an LED, in a plane with the optotype or the test object.

The arrangement of the glare source in the imaging plane of the monitor may provoke undesired reflections in conjunction with the beam splitter. In this regard it is advantageous if the glare source comprises a polariser. By polarising the glare, the reflection thereto is mitigated. If the beam splitter likewise comprises a polariser, it is necessary to arrange the glare source with the polariser on the side of the monitor relative to the beam splitter, since otherwise the polarisation of the beam splitter would block the polarised glare of the glare source.

In order to adjust to one another functions of the components of the eyesight testing apparatus, in particular of the monitor and of the blocking device, it is advantageous if the eyesight testing apparatus comprises a control device with which the relevant components can be controlled. For example, it is thus possible by means of the control device to adapt an image changeover rate of the monitor to a changeover rate of a polarisation device of the LCD blocking elements. Further, for example a motorised adjustment of the eyesight testing apparatus or an automated control and execution of different eyesight tests and evaluation thereof can be achieved by means of the control device.

A particularly high imaging quality of the test object can be achieved if the beam splitter, the deflection device and any deflecting prisms, lenses and any viewing plates provided are broadband-coated.

In a further embodiment of the eyesight testing apparatus, it can be supplemented by a phoropter (i.e., a refractor) or test spectacles. With the phoropter or test spectacles it is thus possible to carry out eyesight tests even if there is insufficient space for optotype projection, for example onto an opposing wall. The phoropter or test spectacles may be mounted rigidly on the eyesight testing apparatus or rigidly connected thereto.

BRIEF DESCRIPTION OF THE DRAWINGS

A preferred embodiment of the invention will be described in greater detail hereinafter with reference to the accompanying drawings, in which.

DETAILED DESCRIPTION OF THE INVENTION

Figure 1:
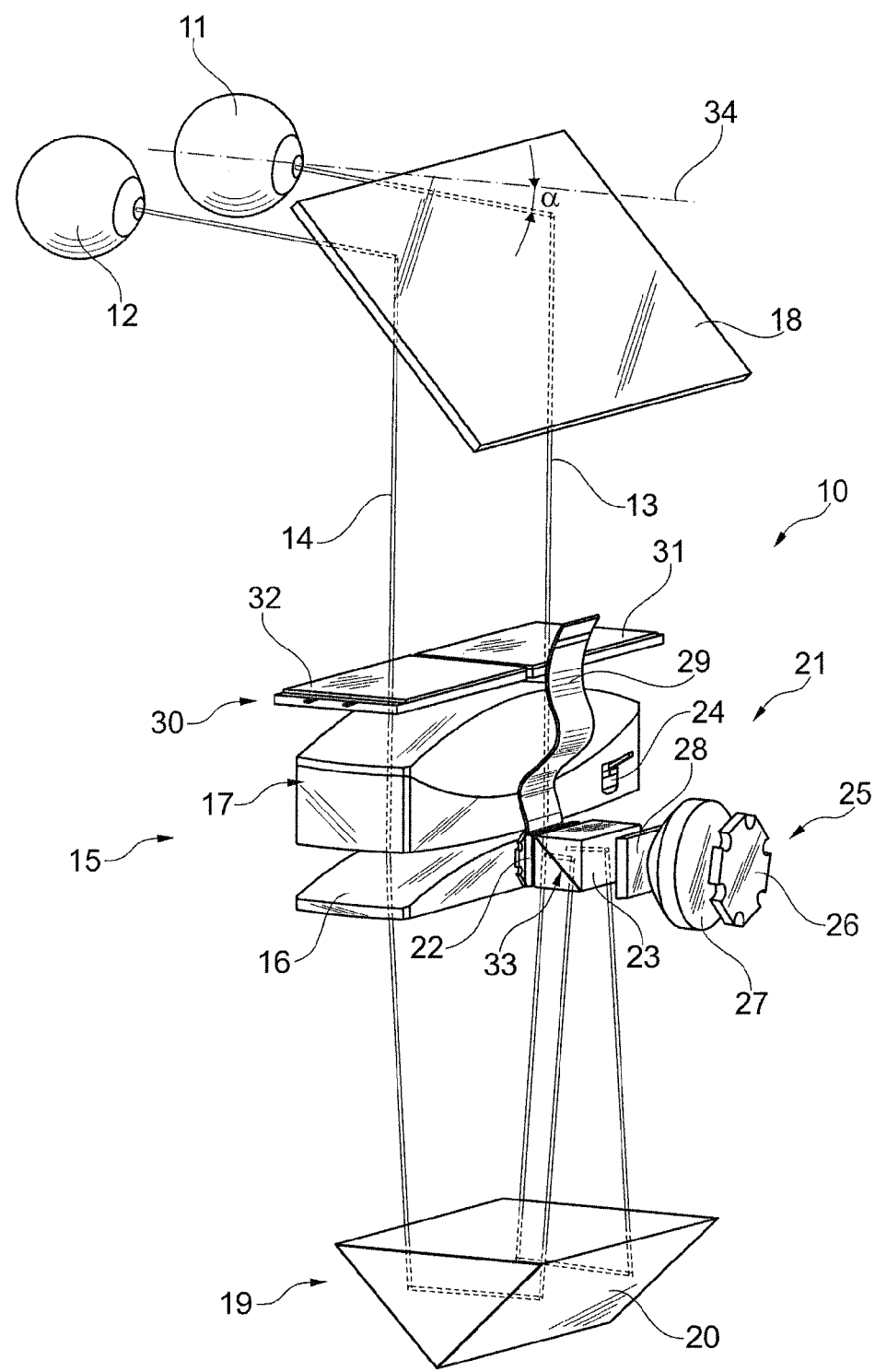
FIG. 1 is a perspective view of optical components of a first illustrative embodiment of an eyesight testing apparatus during a first eyesight test.

FIG. 1 shows an eyesight testing apparatus 10 and the optically effective components thereof that are arranged in a housing (not visible in this instance) of the eyesight testing apparatus 10. A left eye 11 and a right eye 12 of a subject (also not shown in more detail in this instance) are further shown with respective partial beam paths 13 and 14. The eyesight testing apparatus 10 comprises an imaging device 15, formed of a plano-convex lens 16 and an achromatic lens 17 as well as a pivotable deflecting mirror 18. The eyesight testing apparatus 10 further includes a deflection device 19, which comprises a deflecting prism 20 displaceable in the vertical direction. By displacing the deflecting prism 20 it is possible to shorten the partial beam paths 13 and 14, or to adjust the length thereof. The deflecting prism 20 is designed in such a way that the partial beam paths 13 and 14 are deflected by 180°. Furthermore, the eyesight testing apparatus 10 comprises a monitor device 21 that includes an LCD monitor 22, a beam-splitting prism 23, a glare source 24 and an illumination unit 25. The illumination unit 25 is in turn formed of an LED light source 26, a collimator 27 and a diffusing plate 28. A connection line 29 for connecting the LCD monitor 22 to a control device (not shown in this instance) is also illustrated. A blocking device 30 is arranged between the deflecting mirror 18 and the achromatic lens 17 and is formed of two LCD blocking elements 31 and 32 for the partial beam paths 13 and 14 respectively.

With the exception of the blocking device 30, all the aforementioned optical components are of such a size that both eyes 11 and 12 of the subject can simultaneously view the LCD monitor 22 and a test object (not shown in greater detail in this instance) displayed thereon can be imaged in each of the eyes 11 and 12 of the subject. The test object displayed by the LCD monitor 22 is illuminated with incident light by means of the illumination unit 25 and is projected via a deflecting mirror 33 of the beam-splitting prism 23, through the deflecting prism 20, the plano-convex lens 16 and the achromatic lens 17 onto the deflecting mirror 18 and from here into each of the eyes 11 and 12.

Figure 2:
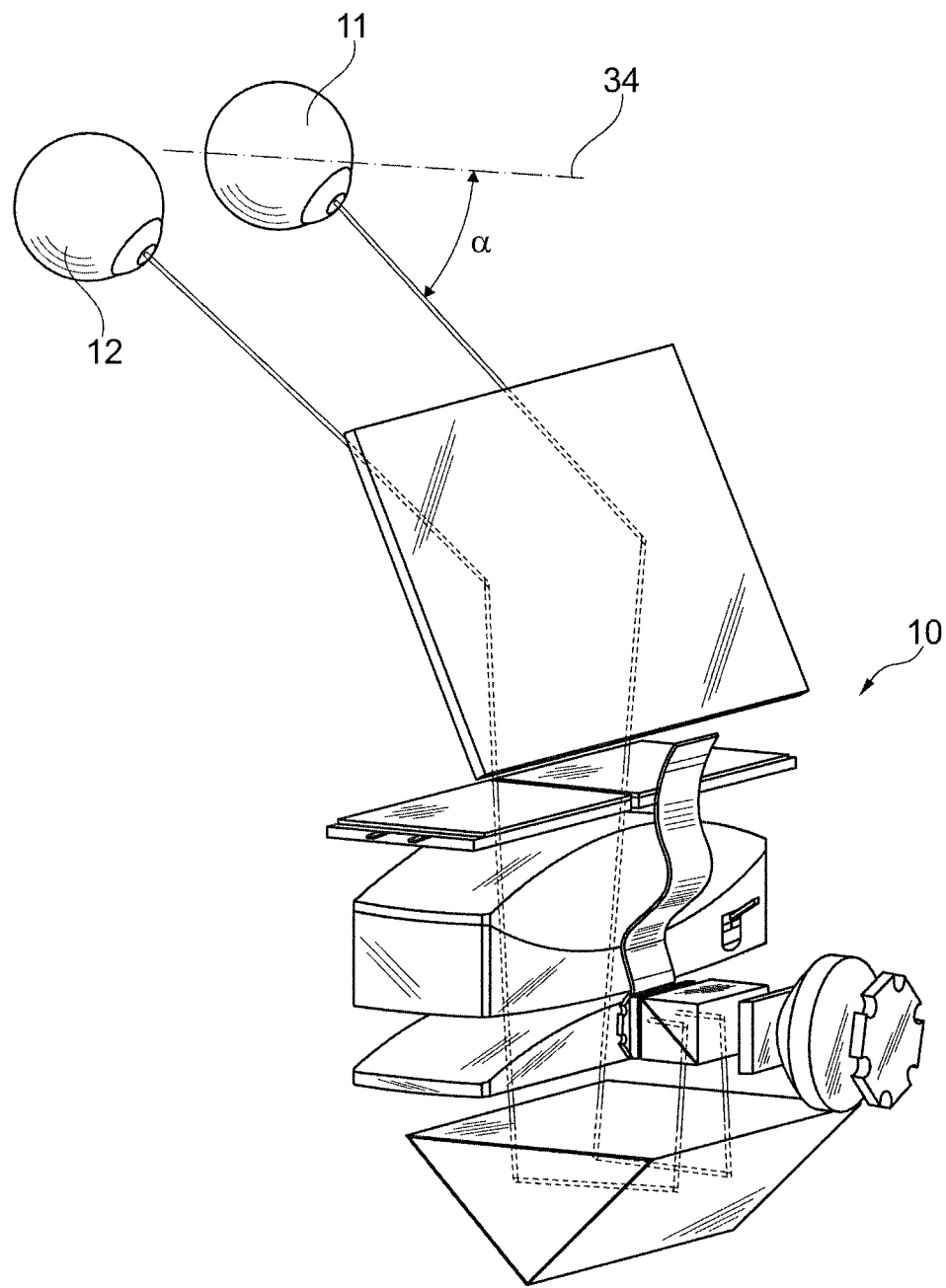
FIG. 2 is a perspective view of the components of the eyesight testing apparatus during a second eyesight test.

By displacing the deflecting prism 20 towards the plano-convex lens 16 and by displacing and rotating the deflecting mirror 18 towards the achromatic lens 17, the partial beam paths 13 and 14, as shown in FIG. 2, are much shortened. The arrangement illustrated in FIG. 1 of the eyesight testing apparatus 10 accordingly shows a test configuration for examining a far vision of the subject, and the test configuration illustrated in FIG. 2 of the eyesight testing apparatus 10 shows an examination of a close vision of the subject. The partial beam paths 13 and starting from the eyes 11 and 12, respectively, are inclined about an angle α in relation to a horizontal optical axis 34 of the subject. In particular, with the test configuration for close vision, the deflecting mirror 18 is lowered until the angle α or the optical axes of the eyes 11 and 12 resulting from the partial beam paths 13 and 14 are approximated with an actual, physiological inclined viewing of the eyes 11 and 12 in the case of close vision. An overall height of the eyesight testing apparatus 10 is thus also reduced to such an extent that a viewing opening (not shown in this instance) in the eyesight testing apparatus 10 is thus lowered in height.

Figure 3:
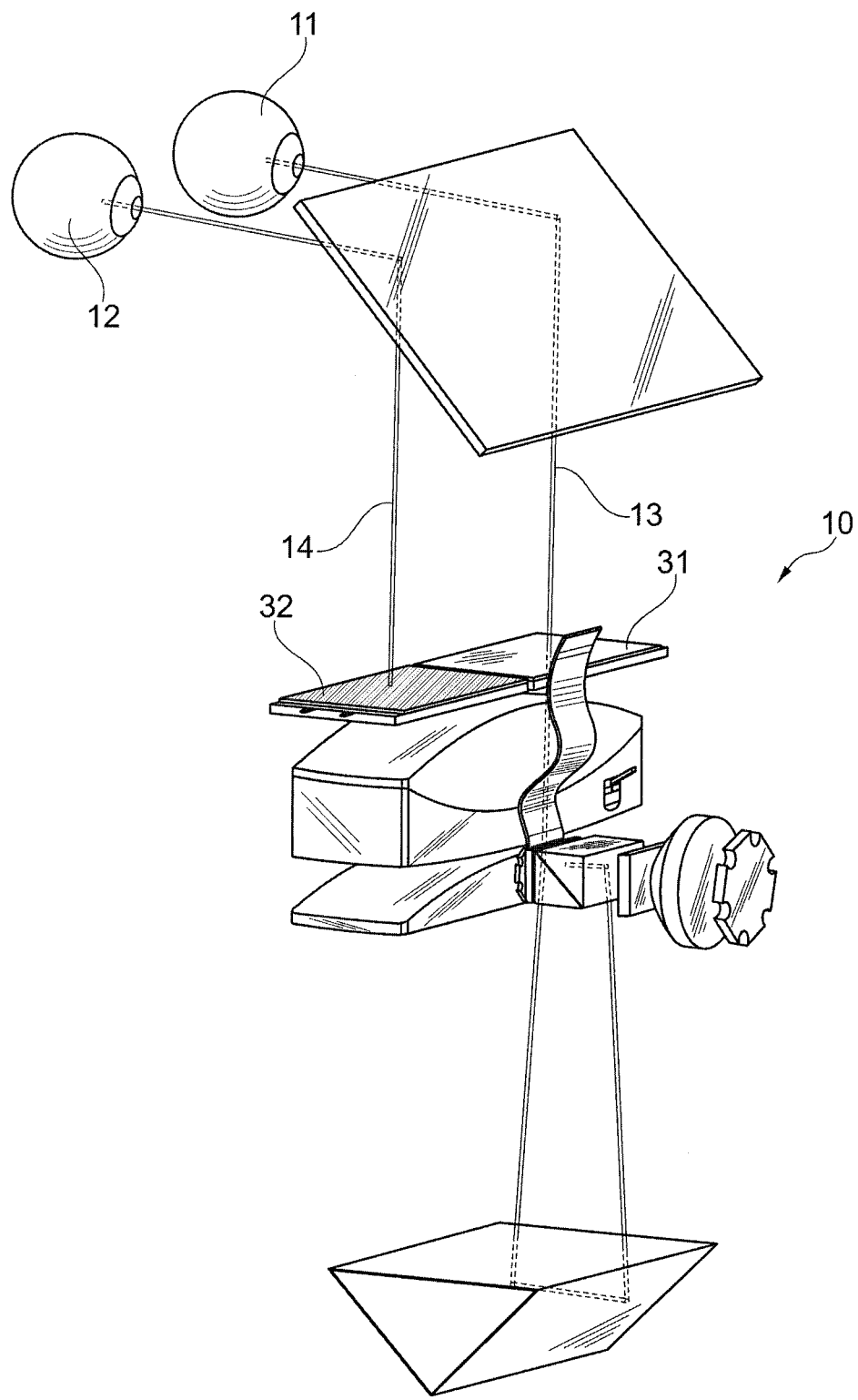
FIG. 3 is a perspective view of the components of the eyesight testing apparatus during a third eyesight test.

FIG. 3 likewise shows the eyesight testing apparatus 10 in a test configuration according to FIG. 1, wherein in this case, in contrast to FIG. 1, the LCD blocking element 32 is shaded or blocked and therefore the partial beam path 14 cannot pass the blocking element 32. An eyesight test is thus merely carried out for the left eye 11. Since the blocking device 30 is arranged inside the housing of the eyesight testing apparatus 10 and cannot be seen directly by the subject, the subject cannot readily determine which of the two eyes 11 or 12 is being tested.

Figure 4:
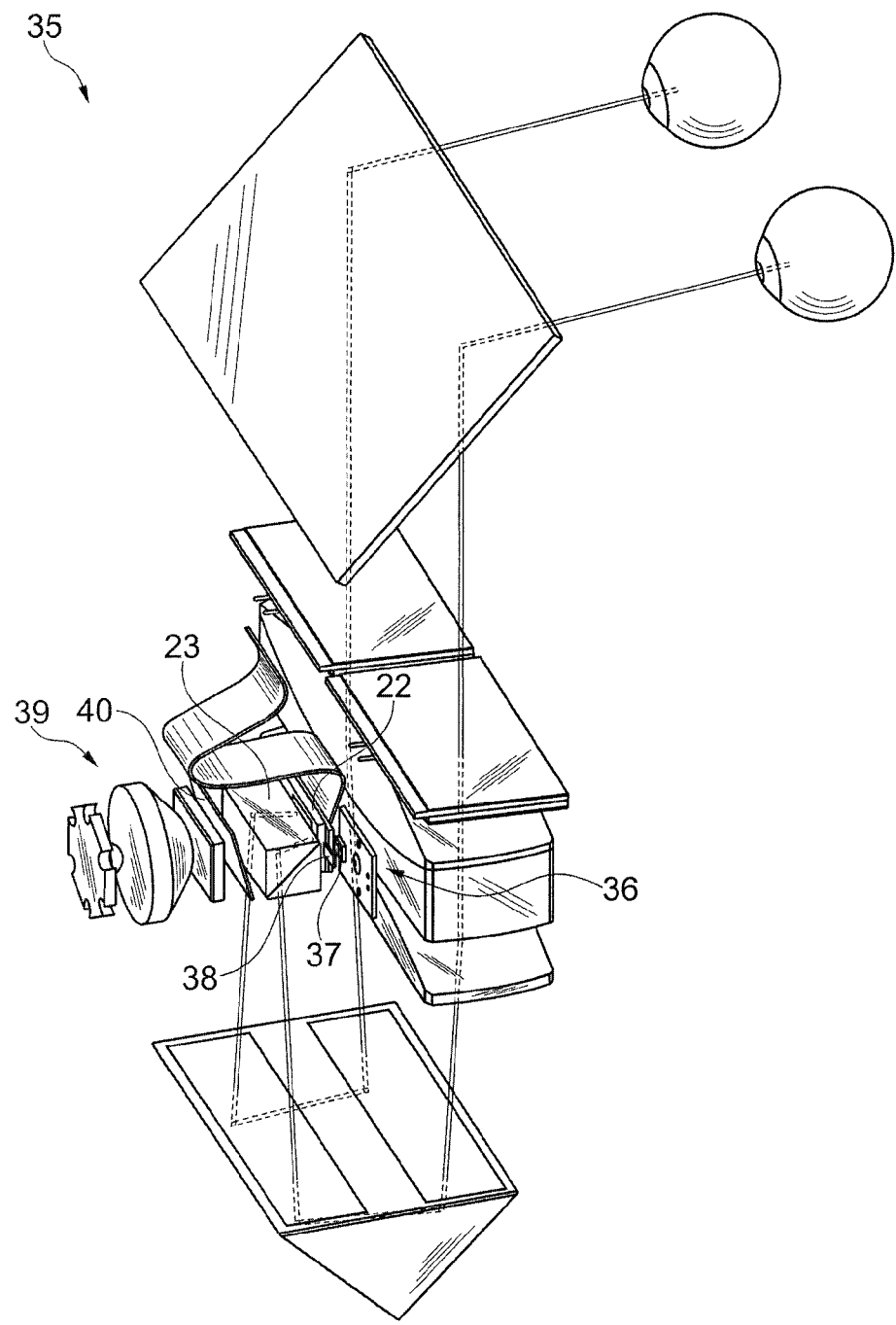
FIG. 4 is a perspective view of optical components of a second illustrative embodiment of an eyesight testing apparatus.

FIG. 4 shows a further embodiment of an eyesight testing apparatus 35. The eyesight testing apparatus 35 basically corresponds to the eyesight testing apparatus shown in FIGS. 1 to 3, with the difference that in the eyesight testing apparatus 35 a glare source 36 comprises an LED 37 having a polariser 38 and is arranged in an imaging plane of the LCD monitor 22. Further, with an illumination unit 39 a polariser 40 is also provided in front of the beam-splitting prism 23. It is thus possible to avoid any undesired reflections caused by the LED 37 and the illumination unit 39.

The invention claimed is:

1. An eyesight testing apparatus comprising:
   (a) an imaging device for virtual imaging of a test object that is located within a focal length of the imaging device and that can be imaged at different distances into eyes of a subject located in a focal point of the imaging device;
   (b) an optical deflection device that is arranged in a first beam path between the imaging device and the test object and the optical deflection device deflects the first beam path by 180 degrees, wherein the optical deflection device is displaceable in the direction of the first beam path, and the test object is not displaceable;
   (c) a monitor device, wherein the monitor device generates the test object, and the monitor device comprises a single monitor and a glare source that can be imaged in the eyes of the subject together with the test object;
   (d) a plurality of optical components lying in the first beam path, wherein each optical component is of such a size that both eyes of the subject are able to take part in a test and so that a partial beam path is formed for each eye; and
   (e) a blocking device is arranged in the first beam path, wherein the blocking device comprises two liquid crystal display blocking elements that are assigned to each of the partial beam paths.

2. The eyesight testing apparatus according to claim 1, wherein each partial beam path can be visually blocked selectively by the blocking device.

3. The eyesight testing apparatus according to claim 1, wherein the single monitor is a liquid crystal display or a light-emitting diode monitor.

4. The eyesight testing apparatus according to claim 1, wherein the imaging device comprises a diverting element for diverting the first beam path.

5. The eyesight testing apparatus according to claim 4, wherein the diverting element is adjustable so that the first beam path incident in the eyes can be inclined relative to a horizontal optical axis of the eyes about an angle α.

6. The eyesight testing apparatus according to claim 4, wherein the blocking device is arranged in the first beam path between the diverting element and a lens group of the imaging device.

7. The eyesight testing apparatus according to claim 1, wherein the monitor device further comprises an illumination unit for the test object.

8. The eyesight testing apparatus according to claim 7, wherein the illumination unit comprises a light-emitting diode light source and a collimator.

9. The eyesight testing apparatus according to claim 8, wherein the light-emitting diode light source comprises at least one red-green-blue-white light-emitting diode.

10. An eyesight testing apparatus comprising:
(a) an imaging device for virtual imaging of a test object that is located within a focal length of the imaging device and that can be imaged at different distances into eyes of a subject located in a focal point of the imaging device;
(b) an optical deflection device that is arranged in a first beam path between the imaging device and the test object and the optical deflection device deflects the first beam path by 180 degrees, wherein the optical deflection device is displaceable in the direction of the first beam path, and the test object is not displaceable;
(c) a monitor device, wherein the monitor device generates the test object, and the monitor device comprises
 i. a single monitor;
 ii. an illumination unit for the test object; and
 iii. a beam splitter that is arranged in the first beam path between the single monitor and the illumination unit;
(d) a plurality of optical components lying in the first beam path, wherein each optical component is of such a size that both eyes of the subject are able to take part in a test and so that a partial beam path is formed for each eye; and
(e) a blocking device is arranged in the first beam path, wherein the blocking device comprises two liquid crystal display blocking elements that are assigned to each of the partial beam paths.

11. The eyesight testing apparatus according to claim 1, wherein the glare source is arranged in an imaging plane of the single monitor.

12. The eyesight testing apparatus according to claim 1, wherein the glare source comprises a polariser.

13. The eyesight testing apparatus according to claim 1, wherein the eyesight testing apparatus further comprises:
(f) a control device operably connected to control the single monitor and the blocking device.

14. The eyesight testing apparatus according to claim 2, wherein two visually different test objects can be displayed at the same time in a discernible manner by the single monitor, wherein the respective partial beam paths are synchronously blockable or releasable by the liquid crystal display blocking elements with a change of a display of the test objects on the single monitor.

15. An eyesight testing apparatus comprising:
(a) an imaging device for virtual imaging of a test object that is located within a focal length of the imaging device and that can be imaged at different distances into eyes of a subject located in a focal point of the imaging device;
(b) an optical deflection device that is arranged in a first beam path between the imaging device and the test object and the optical deflection device deflects the first beam path by 180 degrees, wherein the optical deflection device is displaceable in the direction of the first beam path, and the test object is not displaceable;
(c) a monitor device, wherein the monitor device generates the test object, and the monitor device comprises a single monitor;
(d) a plurality of optical components lying in the first beam path, wherein each optical component is of such a size that both eyes of the subject are able to take part in a test and so that a partial beam path is formed for each eye; and
(e) a blocking device is arranged in the first beam path, wherein the blocking device comprises two liquid crystal display blocking elements that are assigned to each of the partial beam paths, wherein two visually different test objects can be displayed at the same time in a discernible manner by the single monitor, wherein the respective partial beam paths are synchronously blockable or releasable by the liquid crystal display blocking elements with a change of a display of the test objects on the single monitor.

16. An eyesight testing apparatus comprising:
(a) an imaging device for virtual imaging of a test object that is located within a focal length of the imaging device and that can be imaged at different distances into eyes of a subject located in a focal point of the imaging device;
(b) an optical deflection device that is arranged in a first beam path between the imaging device and the test object and the optical deflection device deflects the first beam path by 180 degrees, wherein the optical deflection device is displaceable in the direction of the first beam path, and the test object is not displaceable;
(c) a monitor device, wherein the monitor device generates the test object, and the monitor device comprises a single monitor;
(d) a plurality of optical components lying in the first beam path, wherein each optical component is of such a size that both eyes of the subject are able to take part in a test and so that a partial beam path is formed for each eye; and
(e) a blocking device is arranged in the first beam path, wherein the blocking device comprises two liquid crystal display blocking elements that are assigned to each of the partial beam paths, wherein the imaging device comprises a diverting element for diverting the first beam path and a viewing opening in the eyesight testing apparatus is vertically adjustable relative to an installation surface of the eyesight testing apparatus.

17. The eyesight testing apparatus according to claim 10, wherein the beam splitter forms a polariser.

* * * * *